Jan. 29, 1963 D. E. HENDERSON ET AL Plant Pat. 2,221
GLADIOLUS PLANT
Filed May 3, 1961
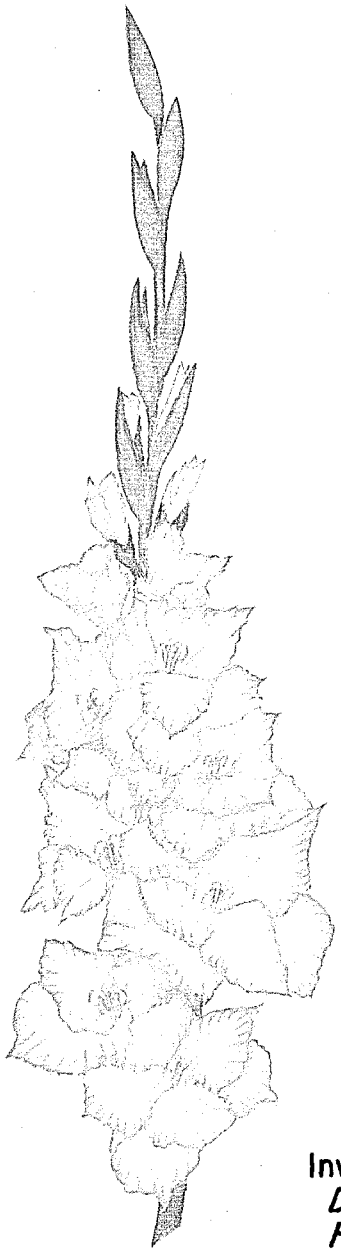
Inventors:
DONALD E. HENDERSON
ROBERT E. WHITE
By: Lamont Johnston
Attorney United States Patent Office Plant Pat. 2,221
Patented Jan. 29, 1963

2,221
GLADIOLUS PLANT

Donald E. Henderson, Lubbock, Tex., and Robert E. White, Waterloo, Iowa, assignors to Selected Glads, Inc., New Albany, Ind., a corporation of Tennessee Filed May 3, 1961, Ser. No. 107,604
1 Claim. (Cl. 47—60)

Our present invention relates to a new and improved variety of gladiolus plant and is notable particularly for its robust growth, unusual coloring, heavy substance and ruffling.

To the best of our knowledge, this new variety is the result of a cross between the varieties White Christmas (unpatented) and Spic and Span (unpatented), White Christmas being the seed parent and Spic and Span the pollen parent. Hand cross-pollination was done by the first-named inventor while living at Waterloo, Iowa, in his field there, but no precaution was taken to prevent admixture of other varieties by bees or insects.

The new variety has been asexually reproduced by both the first-named inventor in his field at Lubbock, Texas, and the second-named inventor in his field at Waterloo, Iowa, by natural increase from cormels through several generations and its characteristics have proven to be permanently fixed.

The illustration, made a part of this application, shows a single bloom spike of this variety, reduced in size, and is as nearly true to color as it is possible to depict. The illustration shows how the florets lie together in semi-formal placement.

In the following detailed description, color plate references are to the "Horticultural Colour Chart," by the British Colour Council. Where there are other references to color, the ordinary dictionary meanings of the terms are intended.

*The Plant*

Growth: Extremely broad fan of erect, broad leaves. Blooming spikes average 52 inches in height over-all. Easy propagator. Cormlets grow into larger sizes of bulbs readily.

Blooming: Each spike opens from seven to eight 5-inch florets at one time. Successive blooms open, to a total of eighteen florets to each spike. The variety is a mid-season bloomer, blooming on the average in 85 days from large bulbs.

Stems: Stocky; diameter at base ¾ inch.

Foliage: Deep green; average leaf is 2½ to 3 inches wide and the plant foliage, excluding the flower spike, is 36 inches tall.

Disease resistance: This variety has been found unusually resistant to Fusarium yellows, Sclerotina dry rot and Septoria leaf spot, to which some other varieties in the fields of the first-named inventor have been subject, observed when grown as a seedling under irrigation in a sandy loam soil in the vicinity of Lubbock, Texas, under the natural conditions provided by the climate of that area. At the end of the season, it would be found that other varieties and seedlings had succumbed or been badly affected, whereas this variety remained healthy and unaffected.

Corms: Round and smooth. Husk is heavy and smooth; flesh is Buttercup Yellow $5/_2$.

*The Flower*

Spike: Tall and heavy with an average of eighteen buds. Opens two to four florets the first day, following which seven to eight are open at one time.

Bud:

*Size.*—Opening buds are 2 to 2½ inches long.

*Opening.*—Five to six will show color at one time.

Flower:

*Arrangement.*—Florets are semi-formally placed in a double row on the stem and usually all face forward.

*Size.*—Individual florets are large, measuring 5 inches in diameter. Upper blooms are progressively smaller.

*Form.*—Wide open, ruffled and triangular. Needle-pointed.

*Keeping qualities.*—Opens well, but flowers sometimes have a smoky cast as they fade.

Petals:

*Size.*—Outer petals are broad, 2¼ inches across; inner petals are 1½ inches across.

*Shape.*—Broad, needle-pointed and extremely ruffled.

*Aspect.*—Substance is leathery; surface is smooth, with corrugation or ruffling at the edges.

*Fragrance.*—None.

*Color.*—The dominant color is Mandarin Red, $17/$ shading to $17/_2$ toward the center and $17/_3$ in the throat. There is a fine picotee edging of Hyacinth Blue, $40/_2$ which is more pronounced as flower fades.

Reproductive organs:

*Stamens.*—Cobalt Violet 634.

*Pistil.*—Mandarin Red $17/_2$.

*Comparisons*

Our new variety resembles Spic and Span (unpatented) more than any other variety, but differs from it principally as follows:

(1) Our variety is larger than Spic and Span.

(2) Our variety is more heavily ruffled than Spic and Span.

(3) Our variety has a much broader fan of leaves and is a healthier plant than Spic and Span.

(4) Our variety has a redder, more unusual color.

(5) Our variety is a better grower from cormlets than Spic and Span.

Having thus disclosed our invention, we claim:

The new and distinct variety of gladiolus plant, substantially as herein shown and described, characterized by its broad fan of leaves, large florets, heavy substance, ruffling, and ease of growth from cormlets.

No references cited.